United States Patent
Allen et al.

(10) Patent No.: US 6,337,408 B1
(45) Date of Patent: Jan. 8, 2002

(54) COMPOUNDS AND METHOD FOR PREPARING SUBSTITUTED 4-PHENYL-4-CYANOCYCLOHEXANOIC ACIDS

(75) Inventors: Andrew Allen, Exton; Ann Marie Diederich, Downingtown; Li Liu, Collegeville; Wilford Mendelson, King of Prussia; Kevin Webb, Phoenixville, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/533,368

(22) Filed: Mar. 22, 2000

Related U.S. Application Data

(63) Continuation of application No. 09/355,786, filed as application No. PCT/US98/02749 on Feb. 12, 1998, now abandoned.
(60) Provisional application No. 60/037,608, filed on Feb. 12, 1997.

(51) Int. Cl.$^7$ .............................................. C07D 303/00
(52) U.S. Cl. ........................ 549/332; 560/59; 558/409; 564/163
(58) Field of Search ........................... 560/59; 564/163; 558/409; 549/332

(56) References Cited

U.S. PATENT DOCUMENTS 5,552,438 A 9/1996 Christensen, IV
5,602,173 A 2/1997 Christensen, IV

FOREIGN PATENT DOCUMENTS

GB 2 144 422 A 3/1985

*Primary Examiner*—Paul J. Killos
(74) *Attorney, Agent, or Firm*—James M. Kanagy; Charles M. Kinzig

(57) ABSTRACT

This invention relates to a method of preparing a compound of the following type

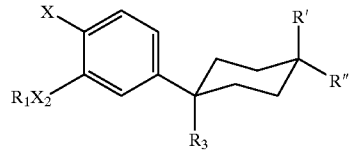

by treating a compound of formula (II)

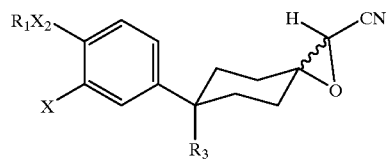

with lithium bromide, magnesium bromide and the like.

26 Claims, No Drawings

COMPOUNDS AND METHOD FOR PREPARING SUBSTITUTED 4-PHENYL-4-CYANOCYCLOHEXANOIC ACIDS

This application is a con of Ser. No. 09/355,786 filed Aug. 4, 1999 now abd, which is a 371 of PCT/US98/02749 filed Feb. 12, 1998 and claims benefit of provisional application Ser. No. 60/037,608 filed Feb. 2, 1997.

SCOPE OF THE INVENTION

This invention covers intermediates and a synthetic route for making 4-cyano-4-(3-cyclopentyloxy-4-methoxyphenyl) cyclohexanoic acid and its analogs. This acid and its named analogs are selective for inhibiting the catalytic site in the phosphodiesterase isoenzyme denominated IV (PDE IV hereafter) and as such the acids are useful in treating a number of diseases which can be moderated by affecting the PDE IV enzyme and its subtypes.

AREA OF THE INVENTION

Bronchial asthma is a complex, multifactorial disease characterized by reversible narrowing of the airway and hyper-reactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3',5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The process and intermediates of this invention provide a means for making certain 4-substituted-4-(3,4-disubstitutedphenyl)cyclohexanoic acids which are useful for treating asthma, and other diseases which can be moderated by affecting the PDE IV enzyme and its subtypes. The final products of particular interest are fully described in U.S. Pat. No. 5,552,483 issues Sep. 3, 1996. The information and representations disclosed therein, in so far are that information and those representations are necessary to the understanding of this invention and in its practice, in total, are incorporated herein by reference.

SUMMARY OF THE INVENTION

This invention relates a method for making a compound of formula I

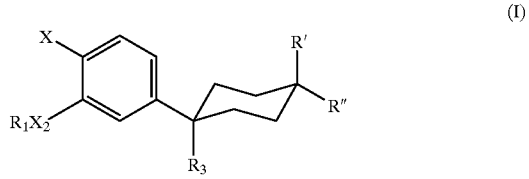

(I)

$R_1$ is $-(CR_4R_5)_nC(O)O(CR_4R_5)_mR_6$, $-(CR_4R_5)_nC(O)NR_4(CR_4R_5)_mR_6$, $-(CR_4R_5)_nO(CR_4R_5)_mR_6$, or $-(CR_4R_5)_rR_6$ wherein the alkyl moieties may be optionally substituted with one or more halogens;

m is 0 to 2;

n is 1 to 4;

r is 0 to 6;

$R_4$ and $R_5$ are independently selected from hydrogen or a $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;

provided that:

a) when $R_6$ is hydroxyl, then m is 2; or b) when $R_6$ is hydroxyl, then r is 2 to 6; or c) when $R_6$ is 2-tetrahydropyranyl, 2-tetrahydrothiopyranyl, 2-tetrahydrofuranyl, or 2-tetrahydrothienyl, then m is 1 or 2; or d) when $R_6$ is 2-tetrahydropyranyl, 2-tetrahydrothiopyranyl, 2-tetrahydrofuranyl, or 2-tetrahydrothienyl, then r is 1 to 6;

e) when n is 1 and m is 0, then $R_6$ is other than H in $-(CR_4R_5)_nO(CR_4R_5)_mR_6$;

X is $YR_2$, halogen, nitro, $NH_2$, or formyl amine;

$X_2$ is O or $NR_8$;

Y is O or $S(O)_{m'}$;

$m'$ is 0, 1, or 2;

$R_2$ is independently selected from —$CH_3$ or —$CH_2CH_3$ optionally substituted by 1 or more halogens;

$R_3$ is hydrogen, halogen, $C_{1-4}$ alkyl, $CH_2NHC(O)C(O)NH_2$, halo-substituted $C_{1-4}$ alkyl, —$CH=CR_{8'}R_{8'}$, cyclopropyl optionally substituted by $R_{8'}$, CN, $OR_8$, $CH_2OR_8$, $NR_8R_{10}$, $CH_2NR_8R_{10}$, $C(Z')H$, $C(O)OR_8$, $C(O)NR_8R_{10}$, or $C\equiv CR_8$;

$R_8$ is hydrogen or $C_{1-4}$ alkyl optionally substituted by one to three fluorines;

$R_{8'}$ is $R_8$ or fluorine;

$R_{10}$ is $OR_8$ or $R_{11}$;

$R_{11}$ is hydrogen, or $C_{1-4}$ alkyl optionally substituted by one to three fluorines;

Z' is O, $NR_9$, $NOR_8$, NCN, $C(—CN)_2$, $CR_8CN$, $CR_8NO_2$, $CR_8C(O)OR_8$, $CR_8C(O)NR_8R_8$, $C(—CN)NO_2$, $C(—CN)C(O)OR_9$, or $C(—CN)C(O)NR_8R_8$;

R' and R" are independently hydrogen or —C(O)OH;

which method comprises treating a compound of formula II(a) or II(b)

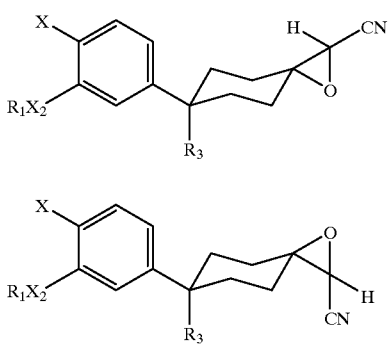

where $R_1$, $R_3$, $X_2$ and X are the same as for formula (I), with lithium bromide or magnesium bromide in a polar solvent at a temperature between about 60° and 100° C., optionally under an inert atmosphere for a time sufficient for the reaction to go to completion.

This invention also relates to compounds of formula II per se.

In another aspect this invention relates to a one-pot method for making the ketone of formula III starting with isovanillin,

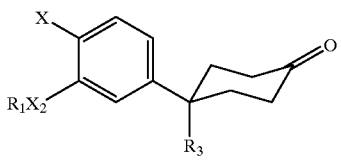

where $R_1$, $R_3$, $X_2$ and X are the same as for formula (I), as more fully described herein below.

In yet a third aspect this invention relates to a process for preparing a compound of formula I which process comprises treating a compound of formula (IV) using an alkali metal cyanide, for example LiCN, in a compatible solvent such as dimethylformamide which contains a small proportion of water

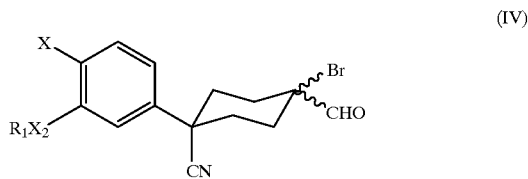

where, in formula III, $R_1$, X and $X_2$ are the same as in formula I.

In a further embodiment this invention relates to a process for making a compound of formula I comprising treating an acyl nitrile of formula V with water.

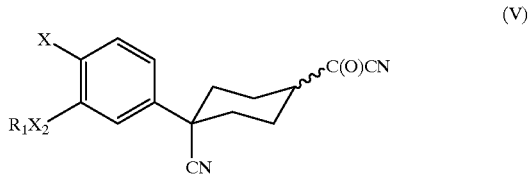

The X, $X_2$ and $R_1$ groups in formula V are the same as those in formula I.

In yet a further embodiment this invention relates to compounds of formula II

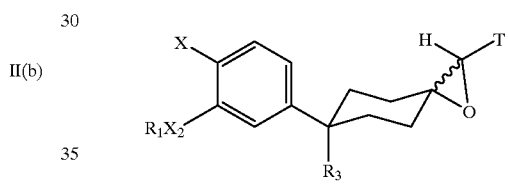

$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties may be optionally substituted with one or more halogens;

m is 0 to 2;

n is 1 to 4;

r is 0 to 6;

$R_4$ and $R_5$ are independently selected from hydrogen or a $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;

provided that:

a) when $R_6$ is hydroxyl, then m is 2; or b) when $R_6$ is hydroxyl, then r is 2 to 6; or c) when $R_6$ is 2-tetrahydropyranyl, 2-tetrahydrofuranyl, or 2-tetrahydrothienyl, then m is 1 or 2; or d) when $R_6$ is 2-tetrahydropyranyl, 2-tetrahydrothiopyranyl, 2-tetrahydrofuranyl, or 2-tetrahydrothienyl, then r is 1 to 6;

e) when n is 1 and m is 0, then $R_6$ is other than H in —$(CR_4R_5)_nO(CR_4R_5)_mR_6$;

X is $YR_2$, halogen, nitro, $NH_2$, or formyl amine;

$X_2$ is O or $NR_8$;

Y is O or $S(O)_{m'}$;

m' is 0, 1, or 2;

$R_2$ is independently selected from —$CH_3$ or —$CH_2CH_3$ optionally substituted by 1 or more halogens;

$R_3$ is hydrogen, halogen, $C_{1-4}$ alkyl, $CH_2NHC(O)C(O)NH_2$, halo-substituted $C_{1-4}$ alkyl, —CH=$CR_{8'}R_{8'}$, cyclopropyl optionally substituted by $R_{8'}$, CN, $OR_8$, $CH_2OR_8$, $NR_8R_{10}$, $CH_2NR_8R_{10}$, $C(Z')H$, $C(O)OR_8$, $C(O)NR_8R_{10}$, or C≡$CR_{8'}$ $R_8$ is hydrogen or $C_{1-4}$ alkyl optionally substituted by one to three fluorines;

$R_{8'}$ is $R_8$ or fluorine;

$R_{10}$ is $OR_8$ or $R_{11}$;

$R_{11}$ is hydrogen, or $C_{1-4}$ alkyl optionally substituted by one to three fluorines;

Z' is O, $NR_9$, $NOR_8$, NCN, $C(—CN)_2$, $R_8CN$, $CR_8NO_2$, $CR_8C(O)OR_8$, $CR_8C(O)NR_8R_8$, $C(—CN)NO_2$, $C(—CN)C(O)OR_9$, or $C(—CN)C(O)NR_8R_8$, and T is CN or $SO_2R$ where R is $C_{1-6}$alkyl or $C_{0-3}$alkylphenyl.

SPECIFIC EMBODIMENTS OF THE INVENTION

This process involves a nine step synthesis for preparing certain 4-substituted-4-(3,4-disubstitutedphenyl)cyclohexanoic acids. The starting material is isovanillin, 3-hydroxy-4-methoxybenzaldehyde, or an analog thereof. "Analog" means another 3 and/or 4 position substituent conforming to the definitions of $R_1$, $R_3$, $X_2$ and X in the definition of formula (I).

The compounds which are made by this process are PDE IV inhibitors. They are useful for treating a number of diseases as described in U.S. Pat. No. 5,552,438 issued Sep. 3, 1996.

The preferred compounds which can be made by this process are as follows:

Preferred $R_1$ substitutents for the compounds of all named formulas are $CH_2$-cyclopropyl, $CH_2$—$C_{5-6}$ cycloalkyl, $C_{4-6}$ cycloalkyl unsubstituted or substituted with $OHC_{7-11}$ polycycloalkyl, (3- or 4-cyclopentenyl), phenyl, tetrahydrofuran-3-yl, benzyl or $C_{1-2}$ alkyl unsubstituted or substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$.

Preferred X groups for Formula (I), (II) or (III) are those wherein X is $YR_2$ and Y is oxygen. The preferred $X_2$ group for Formula (I) is that wherein $X_2$ is oxygen. Preferred $R_2$ groups are a $C_{1-2}$ alkyl unsubstituted or substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Most preferred are those compounds wherein $R_1$ is —$CH_2$-cyclopropyl, cyclopentyl, 3-hydroxycyclopentyl, methyl or $CF_2H$; X is $YR_2$; Y is oxygen; $X_2$ is oxygen; and $R_2$ is $CF_2H$ or methyl; and $R_3$ is CN.

A representative schematic of this process is set out in Scheme I. This graphical representation uses specific examples to illustrate the general methodology used in this invention.

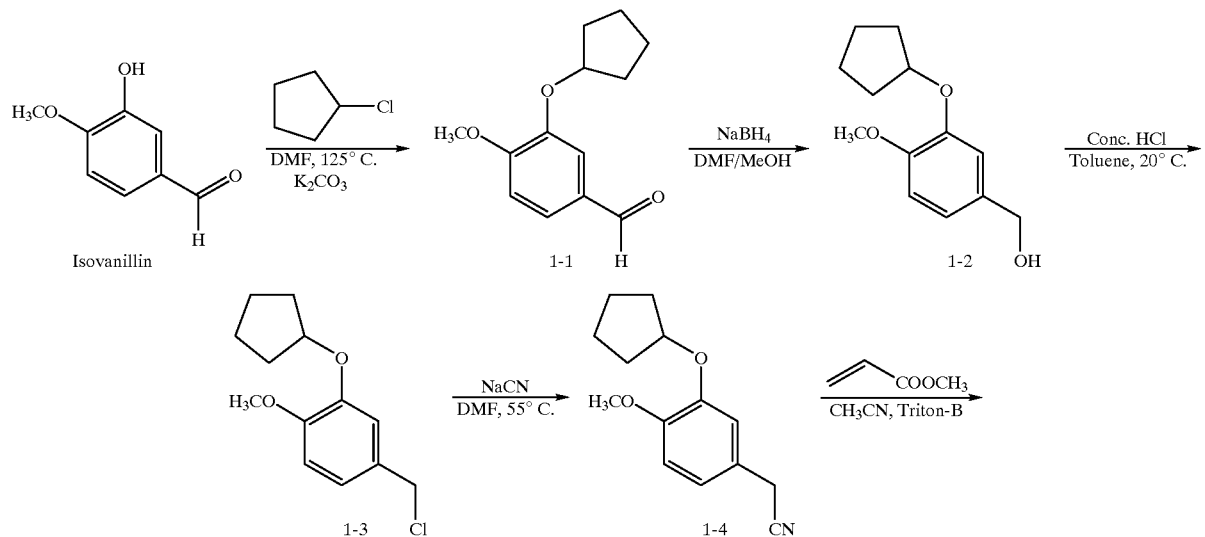

Scheme I

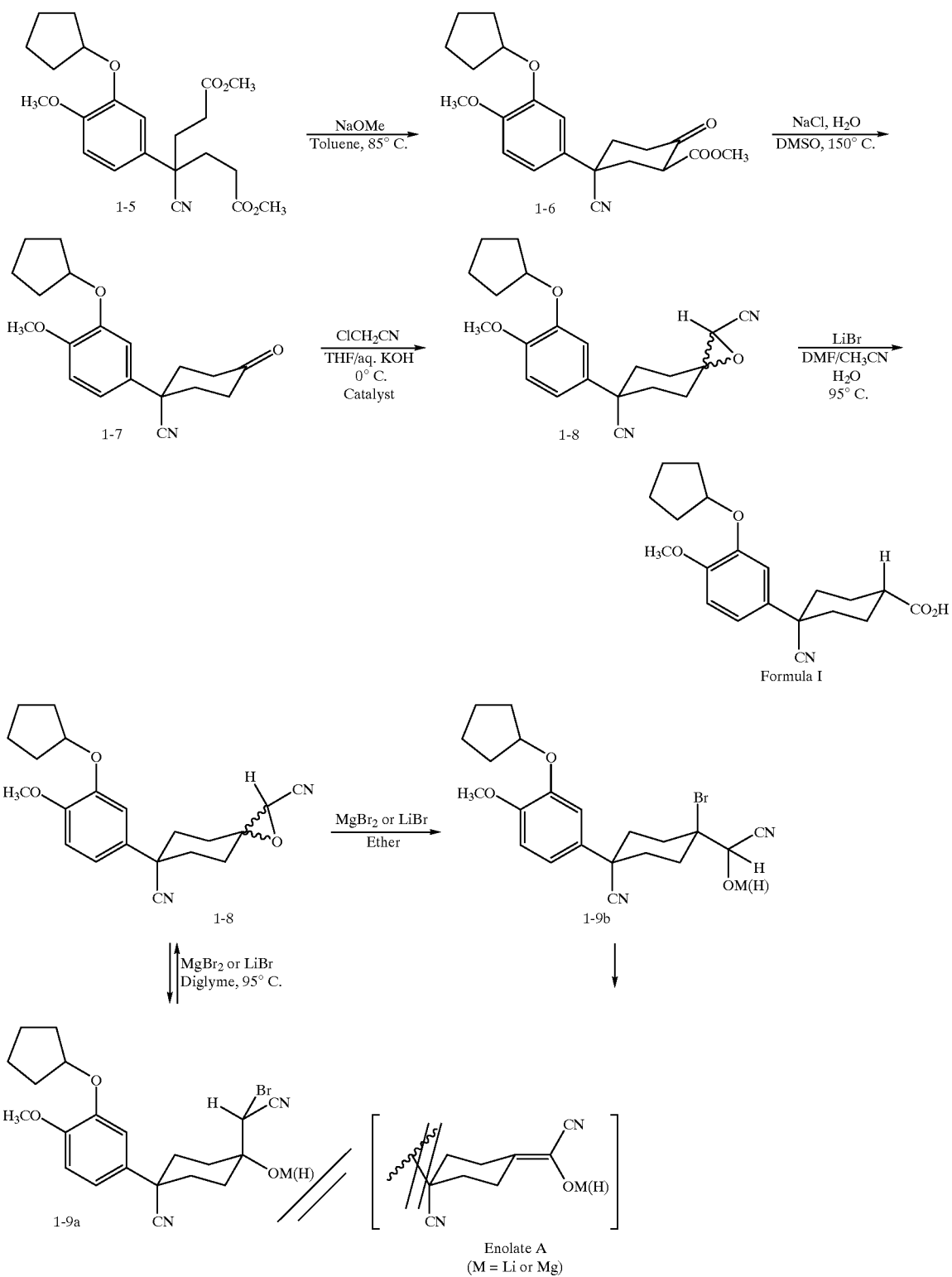

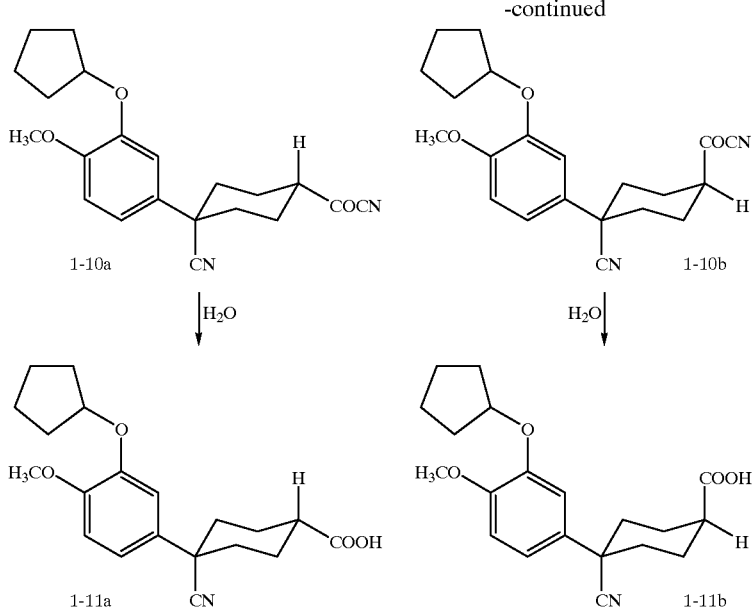

Referring to Scheme I, isovanillin, 3-hydroxy-4-methoxybenzaldehyde, is a readily available starting material. It can be alkylated with an $R_1X$ moiety (X=Cl, Br, and I) as represented by cyclopentyl chloride. The reaction vessel is first flushed with an inert gas, for example nitrogen. A polar solvent such as DMF is then added to the vessel, then the isovanillin, then the $R_1X$ adduct, and some base. About 2 equivalents of the $R_1X$ adduct versus the isovanillin are used. Likewise about 2 equivalents of base are used, again relative to the isovanillin. The base can be any inorganic base or a carbonate. Here it is illustrated by potassium carbonate. The vessel contents are heated to about 125° C. for about 90 to 120 minutes in which time the reaction will have gone to completion. The vessel contents are cooled to ambient temperature, filtered to remove the inorganic salts, and washed with an alcohol such as methanol. This filtrate contains the aldehyde, labeled 1—1.

The aldehyde is then reduced to the alcohol using an inorganic reducing agent. To do this the filtrate from the foregoing reaction is treated with sodium borohydride and after workup affords the desired alcohol, 1-2 in 97% overall yield from isovanillin. This is achieved by cooling the filtrate to about 0° C. after which a reducing agent, here sodium borohydride, is added. About 0.25 to 0.5 equivalents of this reducing agent is used. The temperature is keep at about 0° C. during the addition of the reducing agent and for about 30 to 40 minutes thereafter. Then the temperature is allowed to rise to about room temperature after which about one-half an equivalent of HCl is added to the reaction vessel. The alcohol is then extracted into an organic solvent, toluene is illustrated, and washed with dilute sodium bicarbonate.

The top organic layer containing the alcohol is then treated with excess concentrated hydrochloric acid at ambient temperature to afford, after workup, the desired benzyl chloride 1-3. The chloride is isolated as a w/w solution in an amide solvent, DMF is illustrated, and treated with about a 50% molar excess of sodium cyanide at a mildly elevated temperature, here illustrated as 55° C. This affords the desired nitrile 1-4. The nitrile is isolated as a w/w solution in an appropriate solvent such as anhydrous acetonitrile and used directly in the next step.

The nitrile solution is charged with methyl acrylate. It is cooled to about −10° C., and slowly treated with a catalytic amount of Triton-B in the same solvent as used to dissolve the nitrile. The methyl acrylate is added in a 3 to 4-fold excess. The reaction is complete within 30 to 45 minutes after which the acrylate addition, the pimelate product, 1-5, is isolated as a w/w solution in toluene and treated with about 2 equivalents of sodium methoxide at about 75° C. to give the β-keto-ester product, 1-6. The reaction solution is cooled and neutralized to pH 7 with mineral acid such as 6N hydrochloric acid. The solution is charged with dimethyl sulfoxide, sodium chloride, water, and heated, for example to about 150° C., to effect the decarboxylation to give 1-7. The ketone, 1-7, is isolated from the solvent system as an off-white solid.

The dicarbonitrile 1-8 is prepared from the ketone by treating the ketone with chloroacetonitrile in the presence of an inorganic base and a catalytic amount of benzyltriethylammonium chloride (BTEAC). The ketone is charged into a mixture of strong base (aqueous potassium hydroxide) and a water miscible solvent such as tetrahydrofuran. A slight excess of chloroacetonitrile is added at reduced temperature, about 0° C. or thereabouts. The reaction is maintained at about that temperature for the duration of the reaction, usually about 1 hour. The product is isolated and usually it is crystalline.

The dicarbonitrile is converted to the cyclohexanecarboxylic acid using a Lewis acid catalyst; water is also needed to drive the reaction to the acid. Without water intermediates 1-10a and 1-10b may dimerize. This reaction is carried out by charging a vessel with solvents, in this instance exemplified by DMF, acetonitrile and water, and the Lewis acid (about 1.5 equivalents), LiBr is illustrated, sweeping the vessel with an inert gas, adding the dicarbonitrile IIa or IIb, or a mixture of IIa and IIb and heating the vessel and its contents to about 100° C. for a number of hours, 8 hours being an example. The acid is isolated by conventional means.

It should be noted that this reaction, that is the conversion of the epoxide to the acid, involves several intermediates which do not need to be isolated. It has been found that treating the epoxide with LiBr yields intermediates 1-9a and 1-9b. Intermediate 1-9a is formed when LiBr is added to the reaction pot. But intermediate 1-9a converts back to the epoxide under the recited reaction conditions. Intermediate 1-9b is also formed but apparently reacts rapidly to form intermediates such as enolate A, 1-10a and 1-10b etc leading to product. So it appears 1-9a and 1-9b are formed, but that 1-9a converts back to the epoxide which ultimately forms 1-9b which is then converted to other intermediates enroute to forming the acids of 1-11a and 1-11b. Parenthetically the designation "OM(H)" in 1-9a and 1-9b means the metal salt of the alcohol or the alcohol per se, depending on the reaction conditions. Intermediate 1-9b is believed to convert to the acyl nitrites of formulas 1-10a and 1-10b via the proposed bracketed intermediate. The existence of the proposed bracketed intermediate (enolate) has not been fully confirmed. And while the acyl nitrites of 1-10a and 1-10b have not been directly observed, indirect evidence exists for these compounds by virtue of the fact the bis-condensation product dimer B was isolated and is analogous to reported compounds where a similar bis-condensate is the product of an acyl nitrile.

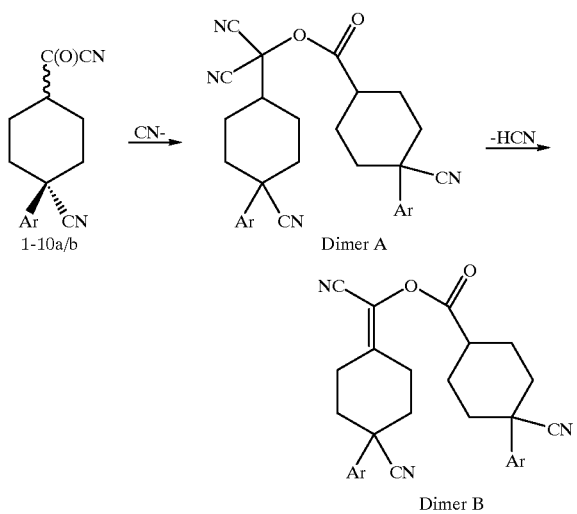

Scheme 2

Dimer A

Dimer B

Dimers such as dimer A are known to form from the likes of acyl nitrites 1-10a/b in the presence of HCN (Thesing, J.; Witzel, D.; Brehm, A. *Angew Chem.*, 1956, 68, 425; and Hunig, S.; Schaller, R. *Angew. Chem. Int. Ed. Engl.*, 1982, 21,36).

And in addition, authentic samples of intermediates 1-10a and 1-10b were prepared and found to convert to acids 1-11a and 1-11b when exposed to water. The equitorial isomer 1-10a converted to the acid in an equitorial/axial ratio of about 98:2 while the axial isomer 1-10a isomerized to a perponderance of the equitorial isomer 1-11a (77:23). It is believed the axial acyl nitrile converts to the equitorial acyl nitrile via the proposed bracketed enolate intermediate.

The second, following reaction scheme illustrates preparing the acids of formula (I) from the bromoaldehyde of formula (IV).

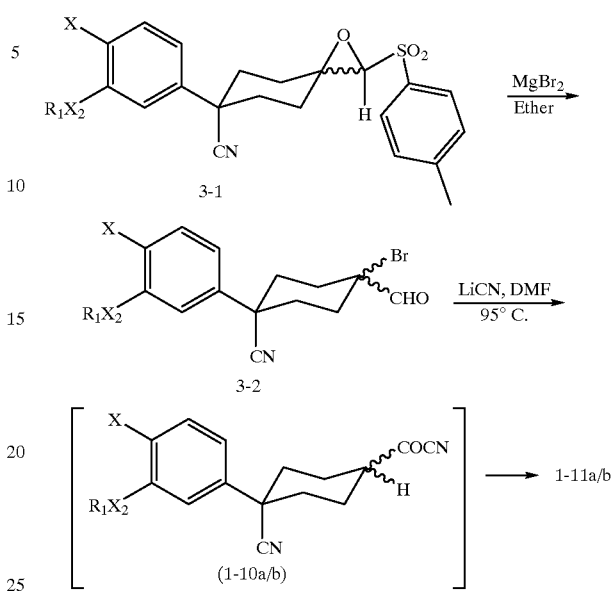

Scheme 3

The following examples are provided to illustrate specifics of the invention, not to limit it. What is reserved to the inventors is set forth in the claims appended hereto.

SPECIFIC EXAMPLES

Example 1
Preparation of 3-cyclopentyloxy-4-methoxybenzaldehyde

A 12 liter round bottom flask equipped with an overhead stirrer, internal thermometer, and a reflux condenser equipped with a nitrogen inlet was flushed with nitrogen. The flask was charged with dimethylformamide (2.4 L), isovanillin (350 g, 2.3 mol, 1 equivalent), cyclopentyl chloride (481 g, 4.6 mol, 2.0 equivalent) and potassium carbonate (634 g, 4.6 mol, 2.0 equivalents). The vigorously stirred suspension was heated to 125° C. for two hours or until the disappearance of isovanillin. The reaction was cooled to 20–30° C. and filtered to remove the inorganic salts. The filter cake was rinsed with methanol (1.0 L).

The clear, light-brown filtrate (DMF and methanol) containing the product, 3-cyclopentyloxy-4-methoxybenzaldehyde, was used directly in the next step (100% solution yield).

Example 2
Preparation of 3-Cyclopentyloxy-4-methoxybenzyl Alcohol

A 12 liter round bottom flask equipped with an overhead stirrer, internal thermometer, and a reflux condensor equipped with a nitrogen inlet was flushed with nitrogen. The flask was charged with dimethylformamide (2.4 L), methanol (1.0 L), and 3-cyclopentyloxy-4-methoxybenzaldehyde (506 g, 2.3 mol, 1 equivalent). The contents of the flask were cooled to 0 to 5° C. followed by the addition of sodium borohydride (32.2 g, 0.85 mol, 0.37 equivalents). The reaction was maintained at 0 to 5° C. for 30 minutes, and warmed to 20 to 25° C. for an additional 2 hours or until the disappearance of the aldehyde. A solution of 6N hydrochloric acid (195 mL, 1.17 mol, 0.51 equivalents) was added over 20 minutes. The reaction was concentrated under reduced pressure, and cooled to 20 to 25° C.

The flask was charged with deionized water (1.9 L) and toluene (1.9 L). The layers were separated, the organic layer was isolated, and washed twice with deionized water (2×800 mL). The product, 3-cyclopentyloxy-4-methoxybenzyl alcohol was collected as a solution in toluene (97% solution yield) and used directly in the next step.

Example 3
Preparation of 4-Chloromethyl-2-cyclopentyloxy-1-methoxybenzene

A 12 liter round bottom flask equipped with an overhead stirrer, internal thermometer, and a reflux condensor equipped with a nitrogen inlet was flushed with nitrogen. The flask was charged with 3-cyclopentyloxy-4-methoxybenzyl alcohol (495 g, 2.2 mol, 1 equivalent) in a solution of toluene. To the vigorously stirred reaction at 22° C. was added concentrated hydrochloric acid (600 g, 2.75 equivalents). The reaction was maintained at 20 to 25° C. for 30 minutes. The top organic layer was isolated and the bottom acidic layer was discarded. To the top organic layer was charged a solution of 10% sodium bicarbonate (550 g, 0.65 mol, 0.36 equivalents) and t-butyl methyl ether (814 g). The contents of the flask were vigorously stirred, and allowed to settle. The product, 4-chloromethyl-2-cyclopentyloxy-1-methoxybenzene, was isolated as a solution in toluene and t-butyl methyl ether (96.8% solution yield). This was used directly in the next step.

Example 4
Preparation of 4-Cyanomethyl-2-cyclopentyloxy-1-methoxybenzene

A 12 liter round bottom flask equipped with an overhead stirrer, and a distillation apparatus was flushed with nitrogen. The flask was charged with 4-chloromethyl-2-cyclopentyloxy-1-methoxybenzene (519 g, 2.15 mol, 1.0 equivalents) in a solution of toluene and t-butyl methyl ether. The reaction was concentrated under reduce pressure to a residue. To the 12 liter flask was charged DMF (1.44 kg) and sodium cyanide (142 g, 2.9 mol, 1.35 equivalents). The reaction was heated to 55° C. for 6 hours or until deemed complete by the disappearance of the benzyl chloride. The reaction was concentrated under reduced pressure to a residue. To the flask was charged t-butyl methyl ether (2.30 kg) and deionized water (800 mL). The contents of the flask were vigorously stirred, and allowed to settle. The top organic layer was isolated, washed three times with deionized water (3×800 mL), and concentrated under atmospheric pressure to a residue. To the flask was added acetonitrile (1.26 kg) and the distillation was continued until an additional 400 mL of solvent was collected. The product, 4-cyanomethyl-2-cyclopentyloxy-1-methoxybenzene, was isolated as a solution in acetonitrile (92.2% yield). This was used directly in the next step.

Example 5
Preparation of Dimethyl-4-cyano-4-(3-cyclopentyloxy-4-methoxy-phenyl)pimelate A 12 liter round bottom flask equipped with an overhead stirrer, internal thermometer, and a reflux condensor equipped with a nitrogen inlet was flushed with nitrogen. The flask was charged with a solution of 4-cyanomethyl-2-cyclopentyloxy-1-methoxybenzene (460 g, 1.99 mol, 1.0 equivalent) in acetonitrile, and methyl acrylate (520 g, 6.0 mol, 3.0 equivalents). The contents of the flask was cooled to −10° C. A pressure equalizing addition funnel was charged with acetonitrile (1.1 L) and benzyltrimethyl ammonium hydroxide (a 40% w/w solution in methanol, 25 g, 0.06 mol, 0.03 equivalents). The contents of the addition funnel was added to the flask. An exotherm was observed, and after stirring for 30 minutes the contents of the flask were cooled to 20° C. The reaction was concentrated under reduced pressure to a residue. To the residue was added toluene (2.6 L). This solution of dimethyl-4-cyano-4-(3-cyclopentyloxy-4-methoxy-phenyl)pimelate(90% solution yield) was used directly in the next step.

Example 6
Preparation of 4-Cyano-4-(3-cyclopentyloxy-4-methoxyphenyl)cyclohexan-1-one A 12 liter round bottom flask equipped with an overhead stirrer, internal thermometer, and a reflux condensor equipped with a nitrogen inlet was flushed with nitrogen. The flask was charged with a solution of dimethyl-4-cyano-4-(3-cyclopentyloxy-4-methoxy-phenyl)pimelate (720 g, 1.78 mol, 1 equivalent) in toluene, and sodium methoxide (25 wt % in methanol, 545 g, 2.67 mol, 1.5 equivalents). The reaction was heated to 70 to 75° C. for 2 hours or until deemed complete by the disappearance of the pimelate. The reaction was cooled to 25° C. A solution of 6N hydrochloric acid was added in order to adjust the pH to 6.8–7.2. The reaction was concentrated under vacuum to a residue. The flask was charged with dimethylsulfoxide (3.3 L), deionized water (250 mL) and sodium chloride (250 g).

The contents of the flask were heated to 145–155° C., and held at this temperature for 2 hours. The reaction was cooled and concentrated under vacuum to a residue. To the residue was added water (1.9 L), ethyl acetate (1.25 L), and t-butyl methyl ether (620 mL). The solution was stirred and allowed to settle. The layers were separated, and the aqueous layer was re-extracted with ethyl acetate (1.25 L). The combined organic layers were washed twice with deionized water (2× 2.5 L). The organic layer was isolated and concentrated under reduced pressure to a residue. To this residue was added isopropanol (1.66 L) and heated to produce a solution followed by the slow addition of hexanes (1.66 L). The suspension was cooled to 5° C. over 30 minutes, and held at 0 to 5° C. for two hours. The product was filtered and washed with 50–50 isopropanol-hexanes (840 mL) mixture at 0° C. The product was dried to afford 4-cyano-4-(3-cyclopentyloxy-4-methoxyphenyl)cyclohexan-1-one (315 g, 56% from the pimelate).

Example 7
Preparation of cis-(±)-6-[3-(cyclopentyloxy)-4-methoxyphenyl]-1-oxobicyclo[2.5]octane-2,6-dicarbonitrile A 5 liter round bottom flask equipped with an overhead stirrer, internal thermometer, and a nitrogen inlet was flushed with nitrogen. The flask was charged with 50% potassium hydroxide (220 g) and tetrahydrofuran (550 mL). While stirring at room temperature, benzyltriethylammonium chloride (8.1 g, 0.035 mol, 0.05 equivalent) was added. The solution was cooled to 0° C. To a pressure equalizing addition funnel was charged a solution containing tetrahydrofuran (550 mL), 4-cyano-4-(3-cyclopentyloxy-4-methoxyphenyl) cyclohexan-1-one (230 g, 0.73 mol, 1.0 equivalent), and chloroacetonitrile (59 g, 0.78 mol, 1.07 equivalent) at room temperature. While stirring the flasks contents at 0° C., the solution in the pressure addition funnel was added over 15 minutes. The temperature was maintained between 0 and 5° C., and stirred for one hour. The reaction was warmed to 25° C., diluted with water (900 mL), and ethyl acetate (900 mL). The solution was stirred and allowed to settle for 30 minutes. The layers were separated, the organic layer was isolated, and concentrated by vacuum distillation to a residue. Methanol (540 mL) was added and the solution was heated to 40° C. While cooling to 20 ° C.

over 90 minutes, hexanes (540 mL) was added. Cooling was continued, and the product began to crystallize at 10° C. The suspension was then cooled to −5° C. and held at −5–0° C. for two hours. The product was filtered and washed with a 50—50 methanol-hexanes mixture (300 mL) at 0 ° C. The product was dried to afford cis-(±)-6-[3-(cyclopentyloxy)-4-methoxyphenyl]-1-oxobicyclo[2.5]octane-2,6-dicarbonitrile (190 g, 73%) as a white crystalline solid.

Example 8

Preparation of 1-9a

In a stoppered 12 dram screw-top vial was added diglyme (5.92 g) and the epoxy nitrile (0.70 g, 1eq) of Example 7. This mixture was stirred with heating in an oil bath for 5 min. Then $MgBr_2.6H_2O$ (0.906 g, 1.55 eq) was added. After 3 hr no starting material was detected. The reaction mixture was cooled, then mixed with 5% aqueous citric acid/ethyl acetate and the layers shaken and separated. The second extraction with ether/ethyl acetate gave some color extracted into organic layer; but the next extraction had no color. The organic fractions were combined and washed with water and brine and dried with $MgSO_4$. The product was crystallized from hexane; mp 151–152° C.

Elemental analysis: C-58.20, H-5,82, Br-18.44, N-6.46; found C-58.32, H-5.73, Br-18.48, N-6.34. The structure was confirmed by X-ray structure determination of a crystalline sample obtained from methyl alcohol.

Example 9

Preparation of 1-9b

To Mg (0.189 g, 2.02 eq) (polished with mortar and pestle) in ether was added 1,2-dibromoethane (1.55 g, 2.06 eq) in a small volume of ether to initiate the Grignard. When most of the magnesium was consumed and no more evolution of ethane was observed, the reaction was stirred for an additional 0.5 hr at room temperature after which was added the epoxide of Example 7 (1.41 g; 1 eq) in a minimal amount of dry tetrahydrofuran at ambient temperature. After about 70 hr at room temperature there was obtained both the bromo cyanoalcohol (1-9b) and bromo cyanohydrin (1-9a) in a ratio of 6:1. The 1-9b product was isolated as an oil by prepartive HPLC. The structure was confirmed by carbon and proton NMR.

Example 10

Preparation of Compound 3-1—Epoxysulfone

To a 25 ml round-bottom flask equipped with a magnetic stir bar and a rubber septum was charged 1.00 g of 4-cyano-4-(3-cyclopentyloxy-4-methoxyphenyl)cyclohexan-1-one, 0.70 g of chloromethyl p-tolylsulfome, and 7 ml of tetrahydrofuran. This was stirred, then 3 ml of 50% w/w aqueous NaOH and benzyltrimeth ch (0.05 g) was added. This suspension was vigorously stirred for 2 hours at room temperature. The reaction solution was transferred to a separatory funnel to which was added 50 ml of ethyl acetate and acidified with 6N HCl. The organic layer was retained, washed 2X with deionized water, dried with $MgSO_4$ and filtered to remove the salts.

Example 11

Preparation of Compound 3-2—Bromoaldehyde

To magnesium (0.048 g, 1.03 eq, 0.021 mol; polished with mortar and pestle) in ether was added 1,2-dibromoethane (0.40 g, 1.06 eq, 0.02 mol) under nitrogen. Two drops of iodine were added in ether to start the reaction, after which the reaction was heated gently. Once the Grignard had formed, the reaction flask was cooled to about 5° C. and the epoxysulfone of Example 10 (0.93 g, 1 eq, 0.002 mol) was added in ether/methylene chloride. The reaction was followed via TLC (conditions: silica gel with cyclohexane-:toluene:acetonitrile:acetic acid 40:40:20:4). The reaction was stirred at 5° for 2 hours. The product was isolated by adding water and ether/TBME to the reaction mixture, and seperating the organic layers. These were washed with water and brine and dried over $MgSO_4$. Evaporation gave an oil which was flash chromatographed over 40 g of silica gel using a mixture of hexane and ethyl acetate (5–40% ethyl acetate). This gave a clear oil (0.49 g) containing about equal proportions of the equitorial and axial isomers as determined by proton NMR. Mass specrum showed a molecular ion at m/e 405 containing 1 bromine atom $[C_{20}H_{24}BrNO_3]$.

Example 12

Preparation of c-4-cyano-4-(3-cyclopentyloxy-4-methoxyphenyl)-r-cyclohexanecarboxylic Acid A 5 liter round bottom flask equipped with an overhead stirrer, internal thermometer, and a reflux condenser equipped with a nitrogen inlet was flushed with nitrogen. The flask was charged with dimethylformamide (580 g), acetonitrile (480 g), lithium bromide (72 g, 0.83 mol, 1.62 equivalents) and deionized water (20 g, 1.1 mol, 2.2 equivalents). The solution was stirred under nitrogen at 25–30° C. followed by the addition of cis-(±)-6-[3-(cyclopentyloxy)-4-methoxyphenyl]-1-oxobicyclo[2.5]octane-2,6-dicarbonitrile (180 g, 0.51 mol, 1.0 equivalent). The reactor was heated to 90–95° C. for 8 hours or until deemed complete by the disappearance of epoxy nitrile. The contents of the flask was cooled to 20° C., followed by the addition of a sodium hydroxide solution (92 g of sodium hydroxide, 2.3 mol, 4.5 equivalents, dissolved in 200 mL of deionized water). The suspension was stirred at 20° C. for 30 minutes followed by the addition of sodium hypochlorite (600 mL, 0.46 mol, 0.9 equivalents). The contents of the flask were stirred for 90 minutes followed by the addition of t-butyl methyl ether (2.27 kg) and 6N HCl (644 mL, 3.86 mol, 7.5 equivalents). The bottom aqueous layer was back-extracted with t-butyl methyl ether (454 g), and the combined organic layer was washed four times with deionized water (4×800 mL). The organic layer was concentrated to a residue. To the flask was charged ethyl acetate (900 g) and heated to reflux. The contents of the flask was cooled to 50° C. followed by the addition of hexanes (672 g). The contents of the flask were cooled to 0° C. and held for 1 hour. The product was filtered and washed with cold ethyl acetate/hexanes (1/9, 175 g). The product was dried to afford c-4-cyano-4-(3-cyclopentyloxy-4-methoxyphenyl)-r-cyclohexanecarboxylic acid (125 g, 69%) as an off-white powder.

Example 13

Preparation of c-4-cyano-4-(3-cyclopentyloxy-4-methoxyphenyl)-r-cyclohexanecarboxylic Acid Chloride In a 1 neck flask equipped for nitrogen flow was combined c-4-cyano-4-(3-cyclopentyloxy-4-methoxyphenyl)-r-cyclohexanecarboxylic acid (1.372 g, 1 eq, 0.004 mol) and oxalyl chloride (4.568 g, 9 eq, 0.036 mol). One drop of dimethyl formamide was then added. This mixture was stirred at ambient temperature overnight. After evaporation under high vacuum this yielded the captioned product.

Example 14

Preparation of Form 1-10a—4-cyano-4-(3-cyclopentyloxy-4-methoxyphenyl)-r-cyclohexane Acyl Nitrile In a flask a sample of the acid chloride (0.217 g, 0.006 mol, 1 eq) prepared in Example 12 was dissolved in $CDCl_3$ (2.34 mL). To this was solution (cooled to 5° C.) was added trimethylsilyl cyanide (0.07 g, 1.3 eq, 0.008 mol.) and a catalytic amount of ZnI$_2$ (0.004 g). This solution was refluxed overnight. This yielded 0.211 g of the captioned product. IR: COCN, ν2220 cm$^{-1}$; C=O, ν1720cm$^{-1}$. The isomeric purity of 1-10a was determined by hydrolyzing the acyl nitrile in warm water, the product being essentially pure compound 1-11a.

Example 15

Preparation of Form 1-10b of 4-cyano-4-(3-cyclopentyloxy-4-methoxyphenyl)-r-cyclohexane Acyl Nitrile In an experiment analogous to Example 14, the axial carboxylic acid was converted to the acid chloride using oxalyl chloride and catalytic amount of dimethyl formamide. This acid chloride was converted directly to the corresponding acyl nitrile, 1-10b, the isomer of the compound prepared in Example 14. The isomeric purity was assayed by hydrolyzing the acyl nitrile by stirring it in warm water for 20 hours. Analytical HPLC determination showed that >96% of the product had the form of 1-10b.

What is claimed is:

1. A method for making a compound of formula I

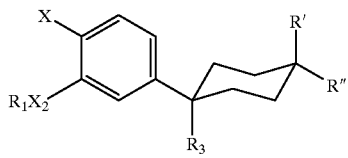

(I)

$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties may be optionally substituted with one or more halogens;

m is 0 to 2;

n is 1 to 4;

r is 0 to 6;

$R_4$ and $R_5$ are independently selected from hydrogen or a $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, C7-11 polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group; provided that:
 a) when $R_6$ is hydroxyl, then m is 2; or
 b) when $R_6$ is hydroxyl, then r is 2 to 6; or
 c) when $R_6$ is 2-tetrahydropyranyl, 2-tetrahydrothiopyranyl, 2-tetrahydrofuranyl, or 2-tetrahydrothienyl, then m is 1 or 2; or
 d) when $R_6$ is 2-tetrahydropyranyl, 2-tetrahydrothiopyranyl, 2-tetrahydrofuranyl, or 2-tetrahydrothienyl, then r is 1 to 6;
 e) when n is 1 and m is 0, then $R_6$ is other than H in —$(CR_4R_5)_nO(CR_4R_5)_mR_6$;

X is $YR_2$, halogen, nitro, $NH_2$, or formyl amine;

$X_2$ is O or $NR_8$;

Y is O or $S(O)_{m'}$;

m' is 0, 1, or 2;

$R_2$ is independently selected from —$CH_3$ or —$CH_2CH_3$ optionally substituted by 1 or more halogens;

$R_3$ is hydrogen, halogen, $C_{1-4}$ alkyl, $CH_2NHC(O)C(O)NH_2$, halo-substituted $C_{1-4}$ alkyl, —CH=$CR_{8'}R_{8'}$, cyclopropyl optionally substituted by $R_{8'}$, CN, $OR_8$, $CH_2OR_8$, $NR_8R_{10}$, $CH_2NR_8R_{10}$, C(Z')H, C(O)$OR_8$, C(O)$NR_8R_{10}$, or C≡$CR_{8'}$;

$R_8$ is hydrogen or $C_{1-4}$ alkyl optionally substituted by one to three fluorines;

$R_{8'}$ is $R_8$ or fluorine;

$R_{10}$ is $OR_8$ or $R_{11}$;

$R_{11}$ is hydrogen, or $C_{1-4}$ alkyl optionally substituted by one to three fluorines;

Z' is O, $NR_9$, $NOR_8$, NCN, C(—CN)$_2$, $CR_8CN$, $CR_8NO_2$, $CR_8C(O)OR_8$, $CR_8C(O)NR_8R_8$, C(—CN)$NO_2$, C(—CN)C(O)$OR_9$, or C(—CN)C(O)$NR_8R_8$;

R' and R" are independently hydrogen or —C(O)OH;

which method comprises treating a compound of formula II

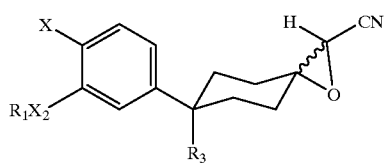

(II)

where $R_1$, $R_3$, $X_2$ and X are the same as for formula (I), with a Lewis acid in a an aqueous solution at a temperature between about 60° and 100° C., optionally under an inert atmosphere for a time sufficient for the reaction to go to completion.

2. The method of claim 1 wherein $R_1X_2$ is cyclopentyloxy and X is methoxy.

3. A compound of formula II

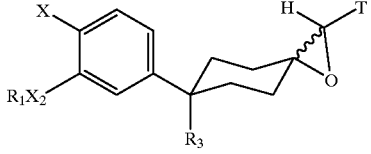

(II)

$R_1$ is —$(CR_4R_5)_nC(O)O(CR_4R_5)_mR6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties may be optionally substituted with one or more halogens;

m is 0 to 2;

n is 1 to 4;

r is 0 to 6;

$R_4$ and $R_5$ are independently selected from hydrogen or a $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;

provided that:
 a) when $R_6$ is hydroxyl, then m is 2; or b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in $-(CR_4R_5)_nO(CR_4R_5)_mR_6$;

X is $YR_2$, halogen, nitro, $NH_2$, or formyl amine;
$X_2$ is O or $NR_8$;
Y is O or $S(O)_{m'}$;
m' is 0, 1, or 2;
$R_2$ is independently selected from $-CH_3$ or $-CH_2CH_3$ optionally substituted by 1 or more halogens;
$R_3$ is hydrogen, halogen, $C_{1-4}$ alkyl, $CH_2NHC(O)C(O)NH_2$, halo-substituted $C_{1-4}$ alkyl, $-CH=CR_{8'}R_{8'}$, cyclopropyl optionally substituted by $R_{8'}$, CN, $OR_8$, $CH_2OR_8$, $NR_8R_{10}$, $CH_2NR_8R_{10}$, C(Z')H, $C(O)OR_8$, $C(O)NR_8R_{10}$, or $C\equiv CR_{8'}$
$R_8$ is hydrogen or $C_{1-4}$ alkyl optionally substituted by one to three fluorines;
$R_{8'}$ is $R_8$ or fluorine;
$R_{10}$ is $OR_8$ or $R_{11}$;
$R_{11}$ is hydrogen, or $C_{1-4}$ alkyl optionally substituted by one to three fluorines;
Z' is O, $NR_9$, $NOR_8$, NCN, $C(-CN)_2$, $CR_8CN$, $CR_8NO_2$, $CR_8C(O)OR_8$, $CR_8C(O)NR_8R_8$, $C(-CN)NO_2$, $C(-CN)C(O)OR_9$, or $C(-CN)C(O)NR_8R_8$, and
T is CN or $SO_2R$ where R is $C_{1-6}$alkyl or $C_{0-3}$alkylphenyl.

4. The compound of claim 3 wherein $R_1X_2$ is cyclopentyloxy and X is methoxy.

5. A process for preparing a compound of formula I(a) or I(b) or a mixture thereof

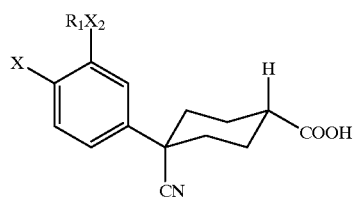

(Ia)

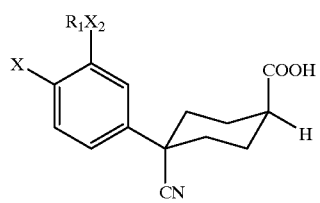

(Ib)

wherein
X is $OR_2$,
$R_2$ is independently selected from $-CH_3$ or $-CH_2CH_3$ optionally substituted by 1 or more halogens;
$R_1$ is $-(CR_4R_5)_rR_6$,
$R_4$ and $R_5$ are independently selected from hydrogen or a $C_{1-2}$ alkyl;
$R_6$ is $C_{3-6}$ cycloalkyl which may be optionally substituted by 1 to 3 methyl groups or one ethyl group; and
$X_2$ is O;
which process comprises treating an acyl nitrile of formula (V) with water

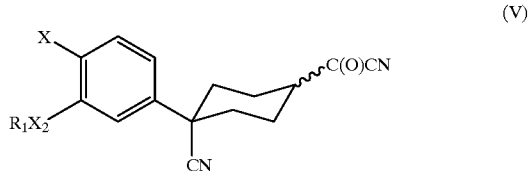

(V)

wherein X and $R_1X_2$ are the same as in formula (Ia) and (Ib).

6. The process of claim 5 wherein the compound of formula (V) is that of formula (Va)

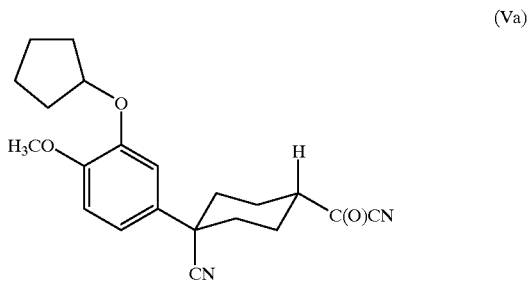

(Va)

and results in the formation of a compound of formula (Ia).

7. The process of claim 5 wherein the compound of formula (V) is that of formula (Vb)

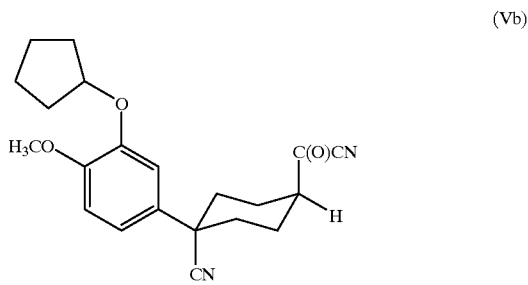

(Vb)

and results in the formation of a compound of formula (Ib).

8. A process for preparing a compound of formula (V)

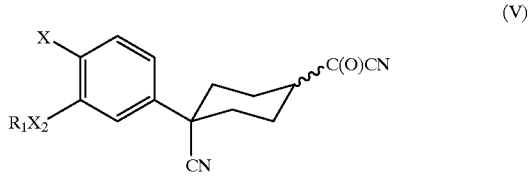

(V)

wherein
X is $OR_2$,
$R_2$ is independently selected from $-CH_3$ or $-CH_2CH_3$ optionally substituted by 1 or more halogens;
$R_1$ is $-(CR_4R_5)_rR_6$,
$R_4$ and $R_5$ are independently selected from hydrogen or a $C_{1-2}$ alkyl;
$R_6$ is $C_{3-6}$ cycloalkyl which may be optionally substituted by 1 to 3 methyl groups or one ethyl group; and
$X_2$ is O;
which process comprises maintaining at about room temperature in solution for a time sufficient to effect the conversion, a compound of formula (Z)

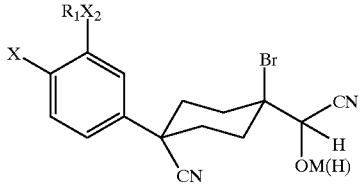

where X and $R_1X_2$ are the same as in formula (V) and M is Li or Mg and the group (H) is hydrogen.

9. The process of claim 8 wherein formula (Z) is that of FIG. 1

FIG. 1

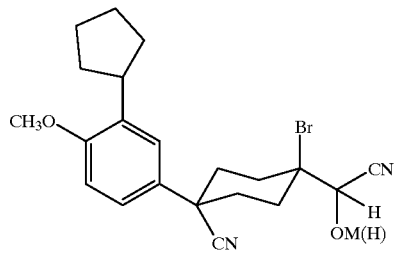

where M is Li or Mg and (H) is hydrogen.

10. A compound of formula (Z)

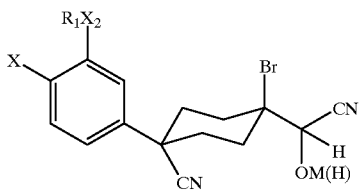

wherein

X is $OR_2$, $R_2$ is independently selected from —$CH_3$ or —$CH_2CH_3$ optionally substituted by 1 or more halogens;

$R_1$ is —$(CR_4R_5)_rR_6$, $R_4$ and $R_5$ are independently selected from hydrogen or a $C_{1-2}$ alkyl;

$R_6$ is $C_{3-6}$ cycloalkyl which may be optionally substituted by 1 to 3 methyl groups or one ethyl group; and $X_2$ is O.

11. A compound of formula (Z) according to claim 10 which is

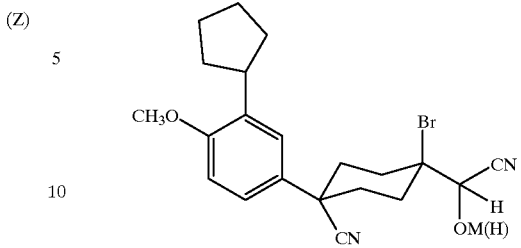

wherein M is Li or Mg and (H) is hydrogen.

12. A process for preparing a compound of formula (Z)

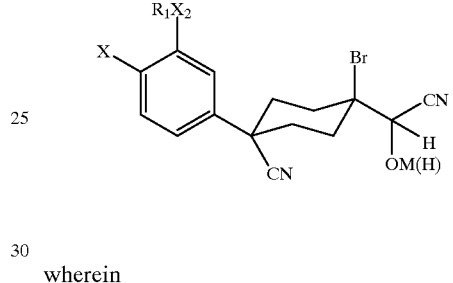

wherein

X is $OR_2$, $R_2$ is independently selected from —$CH_3$ or —$CH_2CH_3$ optionally substituted by 1 or more halogens;

$R_1$ is —$(CR_4R_5)_rR_6$, $R_4$ and $R_5$ are independently selected from hydrogen or a C1-2 alkyl;

$R_6$ is $C_{3-6}$ cycloalkyl which may be optionally substituted by 1 to 3 methyl groups or one ethyl group; and $X_2$ is O;

which process comprises treating an epoxide of formula (II)

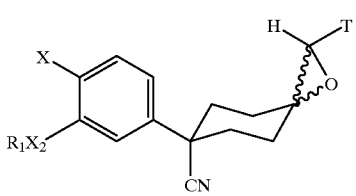

wherein X and $R_1X_2$ are the same as in formula (Z) and T is CN or $SO_2R$ where R is $C_{1-6}$alkyl or $C_{0-3}$alkylphenyl with a Lewis acid under anhydrous conditions.

13. The process of claim 12 wherein the Lewis acid is LiBr.

14. The process of claim 11 or 12 wherein the epoxide of formula (II) has the structure represented by FIG. 2

FIG. 2

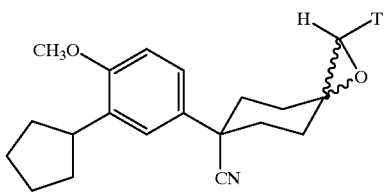

where T is CN or p-tolylsulfonyl.

15. A compound of formula (IV)

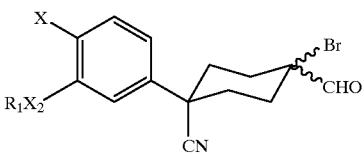

(IV)

where
X is OR$_2$,
R$_2$ is independently selected from —CH$_3$ or —CH$_2$CH$_3$ optionally substituted by 1 or more halogens;
R$_1$ is —(CR$_4$R$_5$)$_r$R$_6$,
R$_4$ and R$_5$ are independently selected from hydrogen or a C$_{1-2}$ alkyl;
R$_6$ is C$_{3-6}$ cycloalkyl which may be optionally substituted by 1 to 3 methyl groups or one ethyl group; and
X$_2$ is O.

16. A compound of formula (IV) according to claim 15 wherein X is methoxy, R$_1$ is cyclopentyl and X$_2$ is oxygen.

17. A process for preparing a compound of formula (Ia) or (Ib)

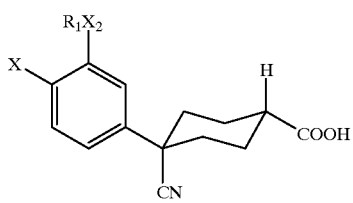

(Ia)

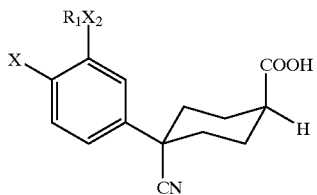

(Ib)

where
X is OR$_2$,
R$_2$ is independently selected from —CH$_3$ or —CH$_2$CH$_3$ optionally substituted by 1 or more halogens;
R$_1$ is —(CR$_4$R$_5$)$_r$R$_6$,
R$_4$ and R$_5$ are independently selected from hydrogen or a C$_{1-2}$ alkyl;
R$_6$ is C$_{3-6}$ cycloalkyl which may be optionally substituted by 1 to 3 methyl groups or one ethyl group; and
X$_2$ is O;

which process comprises treating an aldehyde of formula (IV)

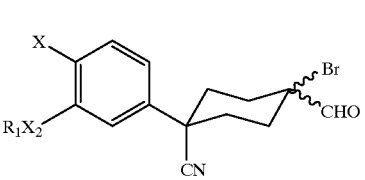

(IV)

wherein X and R$_1$X$_2$ are the same as in formula I(a) and I(b) with an alkali metal cyanide.

18. The process according to claim 17 wherein the cyanide is LiCN.

19. The process according to claim 17 or 18 wherein, in formula (IV), X is methoxy, R$_1$ is cyclopentyl and X$_2$ is oxygen.

20. A process for preparing an acyl nitrile of formula (V)

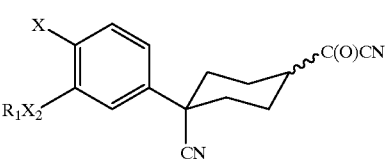

(V)

wherein
X is OR$_2$,
R$_2$ is independently selected from —CH$_3$ or —CH$_2$CH$_3$ optionally substituted by 1 or more halogens;
R$_1$ is —(CR$_4$R$_5$)$_r$R$_6$,
R$_4$ and R$_5$ are independently selected from hydrogen or a C$_{1-2}$ alkyl;
R$_6$ is C$_{3-6}$ cycloalkyl which may be optionally substituted by 1 to 3 methyl groups or one ethyl group; and
X$_2$ is O;
which process comprises treating an aldehyde of formula (IV)

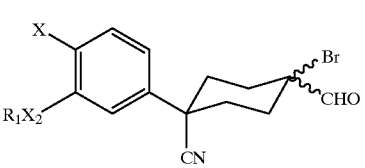

(IV)

wherein X, and R$_1$X$_2$ are the same as in formula (V) with LiCN and a catalytic amount of dimethyl formamide.

21. A compound according to formula (VI)

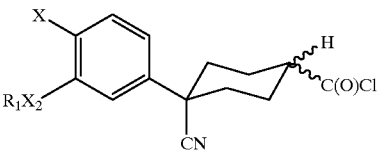

wherein
X is OR$_2$,
R$_2$ is independently selected from —CH$_3$ or —CH$_2$CH$_3$ optionally substituted by 1 or m ore halogens;

R₁ is —(CR₄R₅)ᵣR₆,

R₄ and R₅ are independently selected from hydrogen or a C$_{1-2}$ alkyl;

R₆ is C$_{3-6}$ cycloalkyl which may be optionally substituted by 1 to 3 methyl groups or one ethyl group; and X2 is O.

22. A compound according to claim 21 wherein X is cyclopentyloxy, and R₂ is —CH₃.

23. A process for enriching the c-4-cyano-4-(3-cyclopentyloxy-4-methoxyphenyl)-r-cyclohexanecarboxylic acid form from a mixture of cis and trans isomers of the acid, which process comprises crystallizing from a hexane/ethyl acetate solution of cis and trans isomers the cis isomer essentially free of the trans isomer.

24. The process of claim 23 wherein the cis/trans mixture is dissolved in ethyl acetate and hexanes.

25. The process of claim 24 where the cis/trans mixture is dissolved in ethyl acetate and then hexanes are added.

26. The process of claim 25 wherein the ethyl acetate solution of cis/trans isomers are heated to reflux, cooled and then hexanes added after which crystallization is carried out.

* * * * *